US009241654B2

(12) United States Patent
Edelman

(10) Patent No.: US 9,241,654 B2
(45) Date of Patent: Jan. 26, 2016

(54) SYSTEM AND METHOD FOR SELECTIVE MAGNETIC RESONANCE IMAGING ANGIOGRAPHY OF ARTERIES OR VEINS

(71) Applicant: Robert R. Edelman, Highland Park, IL (US)

(72) Inventor: Robert R. Edelman, Highland Park, IL (US)

(73) Assignee: NORTHSHORE UNIVERSITY HEALTHSYSTEM, Evanston, IL (US)

( * ) Notice: Subject to any disclaimer, the term of this patent is extended or adjusted under 35 U.S.C. 154(b) by 0 days.

(21) Appl. No.: 14/303,761

(22) Filed: Jun. 13, 2014

(65) Prior Publication Data

US 2014/0378826 A1    Dec. 25, 2014

Related U.S. Application Data

(60) Provisional application No. 61/837,403, filed on Jun. 20, 2013.

(51) Int. Cl.
*A61B 5/05* (2006.01)
*A61B 5/055* (2006.01)
*G01R 33/563* (2006.01)
*A61B 5/00* (2006.01)

(52) U.S. Cl.
CPC ............. *A61B 5/055* (2013.01); *A61B 5/004* (2013.01); *G01R 33/5635* (2013.01)

(58) Field of Classification Search
CPC ..... G01R 33/5608; A61B 5/055; A61B 5/004
USPC ........................................ 600/416
See application file for complete search history.

(56) References Cited

U.S. PATENT DOCUMENTS

| 4,973,906 | A | 11/1990 | Bernstein |
| 5,159,550 | A | 10/1992 | Sakamoto et al. |
| 5,492,124 | A | 2/1996 | Purdy |
| 5,652,514 | A | 7/1997 | Zhang et al. |

(Continued)

FOREIGN PATENT DOCUMENTS

WO    2007124244 A1    11/2007

OTHER PUBLICATIONS

Edelman et al., Quiescent-Interval Single-Shot Unenhanced Magnetic Resonance Angiography of Peripheral Vascular Disease: Technical Considerations and Clinical Feasibility, Magnetic Resonance in Medicine 63:951-958, 2010.*

(Continued)

*Primary Examiner* — Long V Le
*Assistant Examiner* — Bo J Peng
(74) *Attorney, Agent, or Firm* — Quarles & Brady, LLP

(57) ABSTRACT

A system and method for producing an image of a vascular structure of a subject using a magnetic resonance imaging (MRI) system includes performing a first pulse sequence to acquire a flow-dependent imaging data set from the stack of prescribed imaging slices following a first quiescent inflow time period (QITP). The process also includes performing a second pulse sequence without suppressing signal from spins flowing into the stack of prescribed imaging slices through either of the veins or arteries to acquire a flow-independent imaging data set. The flow-dependent imaging data and the flow-independent imaging data are subtracted to create a difference image of the stack of prescribed imaging slices illustrating the at least one of the arteries and the veins as having a bright contrast and another of the arteries and veins as having a suppressed contrast.

27 Claims, 4 Drawing Sheets

(56) References Cited

U.S. PATENT DOCUMENTS

| | | | |
|---|---|---|---|
| 5,999,839 | A | 12/1999 | Hardy et al. |
| 6,240,310 | B1 | 5/2001 | Bundy et al. |
| 6,320,377 | B1 | 11/2001 | Miyazaki et al. |
| 7,412,277 | B1 | 8/2008 | Saranathan et al. |
| 8,332,010 | B2 | 12/2012 | Edelman |
| 2002/0032376 | A1 | 3/2002 | Miyazaki et al. |
| 2002/0188190 | A1 | 12/2002 | Kassai et al. |
| 2003/0117136 | A1 | 6/2003 | Wang et al. |
| 2005/0010104 | A1 | 1/2005 | Fayad et al. |
| 2005/0065430 | A1 | 3/2005 | Wiethoff et al. |
| 2006/0184002 | A1 | 8/2006 | Yarnykh et al. |
| 2007/0159174 | A1 | 7/2007 | Oshio |
| 2007/0265522 | A1 | 11/2007 | Kassai et al. |
| 2008/0081987 | A1 | 4/2008 | Miyazaki |
| 2009/0062640 | A1 | 3/2009 | Miyoshi |
| 2010/0268062 | A1* | 10/2010 | Edelman ............ 600/410 |
| 2011/0137146 | A1* | 6/2011 | Edelman ............ 600/410 |
| 2013/0257429 | A1* | 10/2013 | Edelman ............ 324/309 |
| 2014/0018666 | A1* | 1/2014 | Koktzoglou et al. ...... 600/419 |
| 2014/0077807 | A1* | 3/2014 | Edelman et al. ...... 324/309 |
| 2014/0200435 | A1* | 7/2014 | Edelman et al. ...... 600/410 |

OTHER PUBLICATIONS

Hodnett et al., Evaluation of Peripheral Arterial Disease with Nonenhanced Quiescent-Interval Single-Shot MR Angiography, Radiology: vol. 260, No. 1, Jul. 2011.*

Brittain, et al., Three-Dimensional Flow-Independent Peripheral Angiography, Magnetic Resonance in Medicine, 1997, 38:343-354.

Cukur, et al., Signal Compensation and Compressed Sensing for Magnetization-Prepared MR Angiography, IEEE Transactions on Medical Imaging, 2011, 30(5):1017-1027.

Edelman, et al., Fast Time-of-Flight MR Angiography with Improved Background Suppression, Radiology, 1991, 179:867-870.

Edelman, et al., Unenhanced Flow-Independent MR Venography by Using Signal Targeting Alternative Radiofrequency and Flow-Independent Relaxation Enhancement, Radiology, 2009, 250:236-245.

Edelman, et al., Quiescent-Interval Single-Shot Unenhanced Magnetic Resonance Angiography of Peripheral Vascular Disease: Technical Considerations and Clinical Feasibility, Magnetic Resonance in Medicine, 2010, 63 (4):951-958.

Fan, et al., 3D Noncontrast MR Angiography of the Distal Lower Extremities Using Flow-Sensitive Dephasing (FSD)-Prepared Balanced SSFP, Magnetic Resonance in Medicine, 2009, 62:1523-1532.

Fenchel, et al., Multislice First-Pass Myocardial Perfusion Imaging: Comparison of Saturation Recovery (SR)-TrueFISP-Two-Dimensional (2D) and SR-TurboFLASH-2D Pulse Sequences, Journal of Magnetic Resonance Imaging, 2004, 19:555-563.

Francois, et al., Renal Arteries: Isotrophic, High-Spatial-Resolution, Unenhanced MR Angiography with Three-Dimensional Radial Phase Contrast, Radiology, 2011, 258(1):254-260.

Gallix, et al., Flow-Independent Magnetic Resonance Venography of the Calf, Journal of Magnetic Resonance Imaging, 2003, 17:421-426.

Hodnett, et al., Evaluation of Peripheral Arterial Disease with Nonenhanced Quiescent-Interval Single-Shot MR Angiography, Radiology, 2011, 260(1):282-293.

Katoh, et al., Free-Breathing Renal MR Angiography with Steady-State Free-Precession (SSFP) and Slab-Selective Spin Inversion: Initial Results, Kidney International, 2004, 66:1272-1278.

Lim, et al., 3D Nongadolinium-Enhanced ECG-Gated MRA of the Distal Lower Extremities: Preliminary Clinical Experience, Journal of Magnetic Resonance Imaging, 2008, 28:181-189.

Lustig, et al., Sparse MRI: The Application of Compressed Sensing for Rapid MR Imaging, Magnetic Resonance in Medicine, 2007,58:1182-1195.

Miyazaki, et al., A Novel MR Angiography Technique: SPEED Acquisition Using Half-Fourier RARE, Journal of Magnetic Resonance Imaging, 1998, 8:505-507.

Miyazaki, et al., Peripheral MR Angiography: Separation of Arteries from Veins with Flow-Spoiled Gradient Pulses in Electrocardiography-Triggered Three-Dimensional Half-Fourier Fast Spin-Echo Imaging, Radiology, 2003, 227:890-896.

Miyazaki, et al., Nonehanced MR Angiography, Radiology, 2008, 248(1):20-43.

Nakamura, et al., Fresh Blood Imaging (FBI) of Peripheral Arteries: Comparison with 16-Detector Row CT Angiography, Proc. Intl. Soc. Mag. Reson. Med., 2006, 14:1929.

Owen, et al., Magnetic Resonance Imaging of Angiographically Occult Runoff Vessels in Peripheral Arterial Occlusive Disease, New England Journal of Medicine, 1992, 326(24):1577-1581.

Scheffler, et al., Reduced Circular Field-Of-View Imaging, Magnetic Resonance in Medicine, 1998, 40:474-480.

Schreiber, et al., Dynamic Contrast-Enhanced Myocardial Perfusion Imaging Using Saturation-Prepared TrueFISP, Journal of Magnetic Resonance Imaging, 2002, 16:641-652.

Wheaton, et al., Non-Contrast Enhanced MR Angiography: Physical Principles, Journal of Magnetic Resonance Imaging, 2012, 36:286-304.

Wright, et al., Flow-Independent Magnetic Resonance Projection Angiography, Magnetic Resonance in Medicine, 1991, 17:126-140.

Xu, et al., A Novel Non-Contrast MR Angiography Technique Using Triggered Non-Selective Refocused SPACE for Improved Spatial Resolution and Speed, Proc. Intl. Soc. Mag. Reson. Med., 2008, 16:730.

Yamada, et al., Visualization of Cerebrospinal Fluid Movement with Spin Labeling at MR Imaging: Preliminary Results in Normal and Pathophysiologic Conditions, Radiology, 2008; 249:644-652.

Yamashita, et al., Selective Visualization of Renal Artery Using SSFP with Time-Spatial Labeling Inversion Pulse: Non-Contrast Enhanced MRA for Patients with Renal Failure, Proc. Intl. Soc. Mag. Reson. Med., 2005, 13:1715.

* cited by examiner

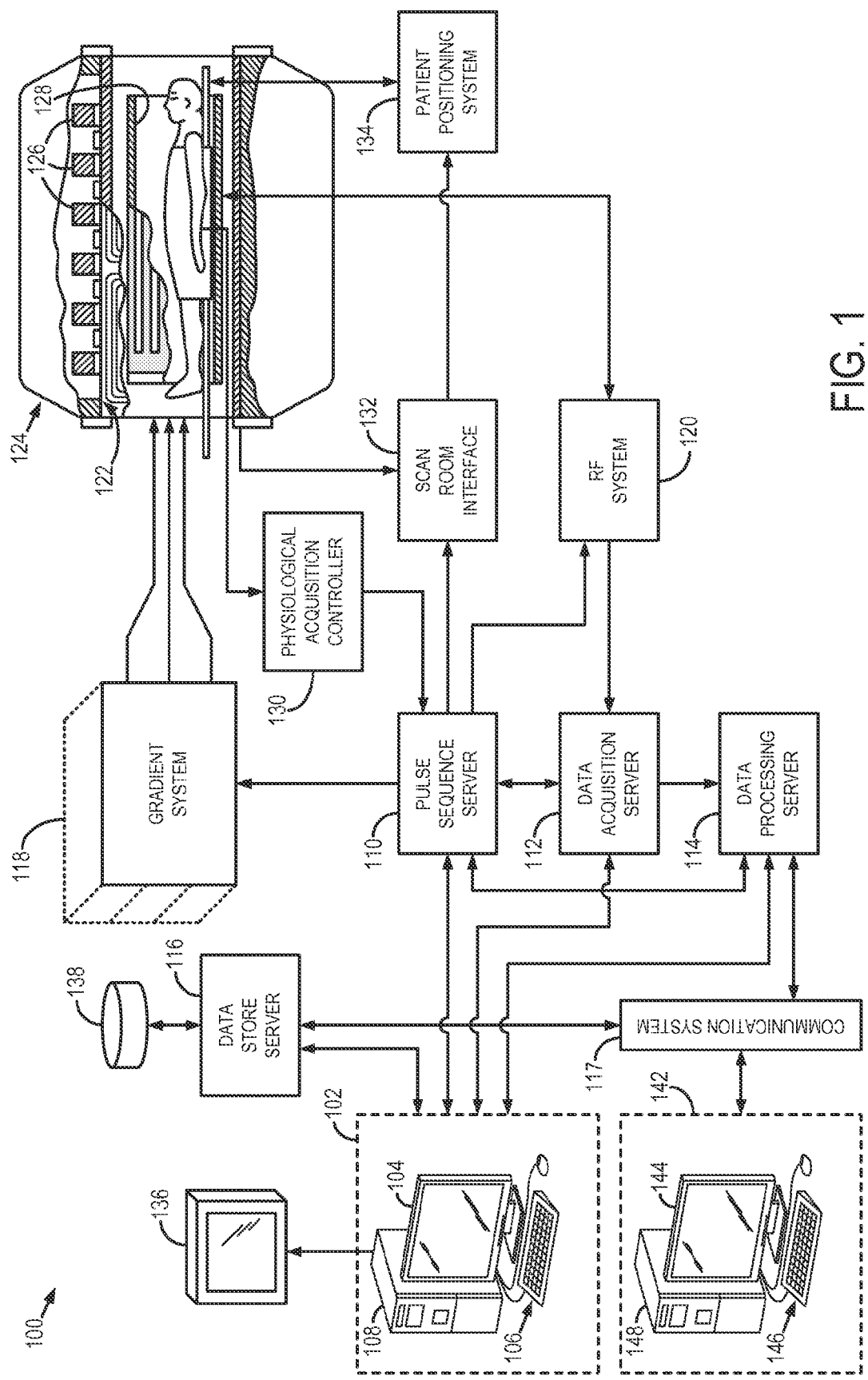

SYSTEM AND METHOD FOR SELECTIVE MAGNETIC RESONANCE IMAGING ANGIOGRAPHY OF ARTERIES OR VEINS

CROSS-REFERENCE TO RELATED APPLICATIONS

This application is based on, claims priority to, and incorporates herein by reference in its entirety, U.S. Provisional Application Ser. No. 61/837,403, filed Jun. 20, 2013, and entitled "SYSTEM AND METHOD FOR SELECTIVE MAGNETIC RESONANCE IMAGING ANGIOGRAPHY OF ARTERIES OR VEINS."

STATEMENT REGARDING FEDERALLY SPONSORED RESEARCH

This invention was made with government support under 1R01HL096916 awarded by National Institutes of Health. The government has certain rights in the invention.

BACKGROUND OF THE INVENTION

The present disclosure relates to magnetic resonance imaging More particularly, the disclosure relates to a system and method for selective imaging of arteries or veins using magnetic resonance imaging.

When a substance such as human tissue is subjected to a uniform magnetic field (polarizing field $B_0$), the individual magnetic moments of the nuclear spins in the tissue attempt to align with this polarizing field, but precess about it in random order at their characteristic Larmor frequency. Usually the nuclear spins are comprised of hydrogen atoms, but other NMR active nuclei are occasionally used. A net magnetic moment $M_z$ is produced in the direction of the polarizing field, but the randomly oriented magnetic components in the perpendicular, or transverse, plane (x-y plane) cancel one another. If, however, the substance, or tissue, is subjected to a magnetic field (excitation field $B_1$; also referred to as the radiofrequency (RF) field) which is in the x-y plane and which is near the Larmor frequency, the net aligned moment, $M_z$, may be rotated, or "tipped" into the x-y plane to produce a net transverse magnetic moment $M_t$, which is rotating, or spinning, in the x-y plane at the Larmor frequency. The practical value of this phenomenon resides in the signal which is emitted by the excited spins after the excitation field $B_1$ is terminated. There are a wide variety of measurement sequences in which this nuclear magnetic resonance ("NMR") phenomenon is exploited.

When utilizing these signals to produce images, magnetic field gradients ($G_x$, $G_y$, and $G_z$) are employed. Typically, the region to be imaged experiences a sequence of measurement cycles in which these gradients vary according to the particular localization method being used. The emitted MR signals are detected using a receiver coil. The MRI signals are then digitized and processed to reconstruct the image using one of many well-known reconstruction techniques.

Magnetic resonance angiography (MRA) and, related imaging techniques, such as perfusion imaging, use the NMR phenomenon to produce images of the human vasculature or physiological performance related to the human vasculature. There are three main categories of techniques for achieving the desired contrast for the purpose of MR angiography. The first general category is typically referred to as contrast enhanced (CE) MRA. The second general category is phase contrast (PC) MRA. The third general category is time-of-flight (TOF) or tagging-based MRA.

Contrast-enhanced MRA (CEMRA) is frequently used to evaluate vascular disease. Although arteries are well evaluated using CEMRA, it is problematic to show veins without troublesome overlap from arteries. Moreover, high contrast doses or a costly blood pool agent may be required. Furthermore, these techniques require the use of exogenous contrast material. Such agents are costly and expose the patient to added safety risks, namely, nephrogenic systemic fibrosis. As such, non-enhanced MRA (NEMRA) techniques are helpful for the evaluation of suspected vascular disease in patients with impaired renal function, since they avoid the risk of nephrogenic systemic fibrosis.

Examples of newer non-enhanced techniques include quiescent-inflow single-shot (QISS) MRA, fresh blood imaging, and flow-sensitive dephasing, such as described in co-pending U.S. application Ser. No. 12/574,856, which is incorporated herein by reference in its entirety. QISS MRA has been shown to be a fast, accurate method for non-contrast MRA. However, imaging of veins can be problematic using traditional QISS techniques due to the intermittent nature of venous flow. In certain regions like the lower-extremities, venous flow may be entirely absent for extended periods of time, so that flow-dependent MRA techniques like QISS do not reliably show venous anatomy.

Additionally, flow-independent MRA techniques are potentially advantageous because they can be implemented as a 3D acquisition with excellent signal-to-noise ratio, high spatial resolution, and insensitivity to abnormal flow patterns. Flow-independent MRA techniques can be performed during the steady-state, after administration of a blood pool contrast agent, such as gadofosveset trisodium, or can be acquired without contrast agents using pulse sequences such as 3D balanced steady-state free precession. However, the projective images overlap between arteries and veins severely limits the diagnostic utility of images acquired using flow-independent MRA. Attempts have been made to suppress venous or arterial signal by applying a saturation pulse outside of the imaging region. However, the saturation pulse is ineffective because, unlike the case with thin, 2D slices, inflowing saturated blood undergoes T1 relaxation and substantially recovers its signal intensity before it penetrates far into a large, 3D volume.

Thus, it would be desirable to have a system and method for non-contrast-enhanced imaging arteries and veins and/or flow-independent MRA imaging techniques that do not suffer from the challenges set forth above and other challenges.

SUMMARY OF THE INVENTION

The present disclosure overcomes the aforementioned drawbacks by providing a system and method for non-enhanced, magnetic resonance angiography for creating two sets of angiographic data that can be combined, for example, using subtraction, to selectively yield images that depict only arteries or only veins. The disclosure further provides a system and method for flow-independent MRA, acquired with or without contrast enhancement, to selectively depict arteries or veins.

In accordance with one aspect of the disclosure, a magnetic resonance imaging (MRI) system is provided that includes a magnet system configured to generate a polarizing magnetic field about at least a region of interest (ROI) in a subject arranged in the MRI system. The MRI system also includes a plurality of gradient coils configured to apply a gradient field to the polarizing magnetic field and a radio frequency (RF) system configured to apply an excitation field to the subject and acquire MR image data from a ROI. The MRI system also includes a computer system programmed to carry out steps of a) performing a first pulse sequence that directs the MRI system to i) apply at least one RF saturation pulse to a prescribed imaging slice to substantially suppress MR signals in the prescribed imaging slice. The MRI system is also directed to ii) apply at least one RF saturation pulse to a slice outside the prescribed imaging slice to suppress signal from spins flowing into the prescribed imaging slice from the slice outside the prescribed imaging slice through one of veins and arteries, iii) observe a first quiescent inflow time period (QITP) selected to allow a desired inflow of spins flowing into the prescribed imaging slice from the slice outside the prescribed imaging slice through the one of arteries and veins, and iv) acquire a flow-dependent imaging data set from the prescribed imaging slice following the first QITP. The computer system is further programmed to carry out steps of b) performing a second pulse sequence that directs the MRI system to acquire a flow-independent imaging data set from the prescribed imaging slice. The computer system is further programmed to carry out the steps of c) subtracting the flow-dependent imaging data and the flow-independent imaging data to create a difference image of the prescribed imaging slice. The MRI system also includes a display configured to display the image of the prescribed imaging slice illustrating the at least one of the arteries and the veins as having a bright contrast and another of the arteries and veins as having a suppressed contrast.

In accordance with another aspect of the disclosure, a method is provided for producing an image of a vascular structure of a subject using a magnetic resonance imaging (MRI) system. The method includes a) performing a first pulse sequence that directs the MRI system to i) apply at least one radio frequency (RF) saturation pulse to a prescribed imaging slice to substantially suppress MR signals in the prescribed imaging slice and ii) apply at least one RF saturation pulse to a slice outside the prescribed imaging slice to suppress signal from spins flowing into the prescribed imaging slice from the slice outside the prescribed imaging slice through one of veins and arteries. The MRI system is further directed to iii) observe a first quiescent inflow time period (QITP) selected to allow a desired inflow of spins flowing into the prescribed imaging slice from the slice outside the prescribed imaging slice through the one of arteries and veins and iv) acquire a flow-dependent imaging data set from the prescribed imaging slice following the first QITP. The method also includes b) performing a second pulse sequence that directs the MRI system to i) apply at least one RF saturation pulse to a slice outside the prescribed imaging slice to suppress signal from spins flowing into the prescribed imaging slice from the slice outside the prescribed imaging slice through a one of arteries and veins not saturated in step a)ii) and ii) observe a second QITP selected to allow a desired inflow of spins flowing into the prescribed imaging slice from the slice outside the prescribed imaging slice through the one of arteries and veins not saturated in step a)ii). The MRI system is further directed to iii) acquire a flow-independent imaging data set from the prescribed imaging slice following the second QITP. The method also includes c) subtracting the flow-dependent imaging data and the flow-independent imaging data to create a difference image of the prescribed imaging slice and d) displaying the image of the prescribed imaging slice illustrating the at least one of the arteries and the veins as having a bright contrast and another of the arteries and veins as having a suppressed contrast.

In accordance with yet another aspect of the disclosure, a method for is disclosed for producing an image of a vascular structure of a subject using a magnetic resonance imaging (MRI) system. The method includes a) performing a first pulse sequence that directs the MRI system to i) determine a stack of prescribed imaging slices including arteries and veins and ii) apply a series of RF saturation pulses to slices outside the each slice in the stack of prescribed imaging slices to suppress signal from spins flowing into the stack of prescribed imaging slices through one of veins and arteries. The MRI system is further directed to iii) observe a first quiescent inflow time period (QITP) selected to allow an inflow of suppressed signals from spins flowing into the stack of prescribed imaging slices through the one of arteries and veins and iv) acquire a flow-dependent imaging data set from the stack of prescribed imaging slices following the first QITP. The method also includes b) repeating step a) without suppressing signal from spins flowing into the stack of prescribed imaging slices through either of the veins or arteries to acquire a flow-independent imaging data set after a second QITP. The method further includes c) subtracting the flow-dependent imaging data and the flow-independent imaging data to create a difference image of the prescribed imaging slice and d) displaying the image of the stack of prescribed imaging slices illustrating the at least one of the arteries and the veins as having a bright contrast and another of the arteries and veins as having a suppressed contrast.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 1 is a schematic diagram of a magnetic resonance imaging system configured for use with the present disclosure.

DETAILED DESCRIPTION OF THE INVENTION

Figure 2A:
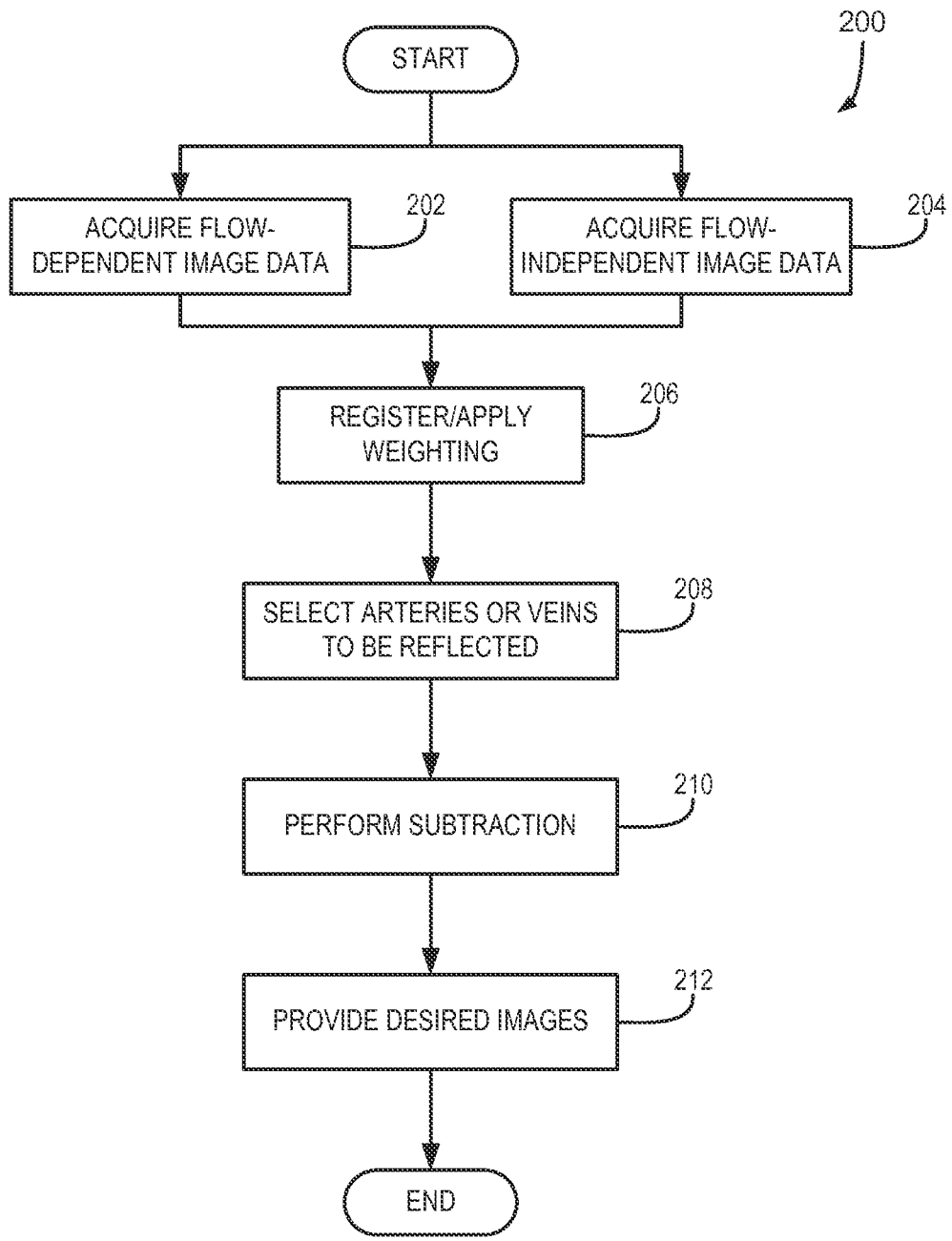
FIG. 2A is a flow chart setting forth the steps of an imaging process in accordance with the present disclosure, for example, using a system such as described with respect to FIG. 1.

Referring particularly now to FIG. 1, an example of a magnetic resonance imaging (MRI) system 100 is illustrated. The MRI system 100 includes an operator workstation 102, which will typically include a display 104, one or more input devices 106, such as a keyboard and mouse, and a processor 108. The processor 108 may include a commercially available programmable machine running a commercially available operating system. The operator workstation 102 provides the operator interface that enables scan prescriptions to be entered into the MRI system 100. In general, the operator workstation 102 may be coupled to four servers: a pulse sequence server 110; a data acquisition server 112; a data processing server 114; and a data store server 116. The operator workstation 102 and each server 110, 112, 114, and 116 are connected to communicate with each other. For example, the servers 110, 112, 114, and 116 may be connected via a communication system 117, which may include any suitable network connection, whether wired, wireless, or a combination of both. As an example, the communication system 117 may include both proprietary or dedicated networks, as well as open networks, such as the internet.

The pulse sequence server 110 functions in response to instructions downloaded from the operator workstation 102 to operate a gradient system 118 and a radiofrequency ("RF") system 120. Gradient waveforms necessary to perform the prescribed scan are produced and applied to the gradient system 118, which excites gradient coils in an assembly 122 to produce the magnetic field gradients $G_x$, $G_y$, and $G_z$ used for position encoding magnetic resonance signals. The gradient coil assembly 122 forms part of a magnet assembly 124 that includes a polarizing magnet 126 and a whole-body RF coil 128.

RF waveforms are applied by the RF system 120 to the RF coil 128, or a separate local coil (not shown in FIG. 1), in order to perform the prescribed magnetic resonance pulse sequence. Responsive magnetic resonance signals detected by the RF coil 128, or a separate local coil (not shown in FIG. 1), are received by the RF system 120, where they are amplified, demodulated, filtered, and digitized under direction of commands produced by the pulse sequence server 110. The RF system 120 includes an RF transmitter for producing a wide variety of RF pulses used in MRI pulse sequences. The RF transmitter is responsive to the scan prescription and direction from the pulse sequence server 110 to produce RF pulses of the desired frequency, phase, and pulse amplitude waveform. The generated RF pulses may be applied to the whole-body RF coil 128 or to one or more local coils or coil arrays (not shown in FIG. 1).

The RF system 120 also includes one or more RF receiver channels. Each RF receiver channel includes an RF preamplifier that amplifies the magnetic resonance signal received by the coil 128 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M=\sqrt{I^2+Q^2} \qquad \text{Eqn. 1;}$$

and the phase of the received magnetic resonance signal may also be determined according to the following relationship:

$$\varphi = \tan^{-1}\left(\frac{Q}{I}\right). \qquad \text{Eqn. 2}$$

The pulse sequence server 110 also optionally receives patient data from a physiological acquisition controller 130. By way of example, the physiological acquisition controller 130 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 110 to synchronize, or "gate," the performance of the scan with the subject's heart beat or respiration.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized magnetic resonance signal samples produced by the RF system 120 are received by the data acquisition server 112. The data acquisition server 112 operates in response to instructions downloaded from the operator workstation 102 to receive the real-time magnetic resonance data and provide buffer storage, such that no data is lost by data overrun. In some scans, the data acquisition server 112 does little more than pass the acquired magnetic resonance data to the data processor server 114. However, in scans that require information derived from acquired magnetic resonance data to control the further performance of the scan, the data acquisition server 112 is programmed to produce such information and convey it to the pulse sequence server 110. For example, during prescans, magnetic resonance data is acquired and used to calibrate the pulse sequence performed by the pulse sequence server 110. As another example, navigator signals may be acquired and used to adjust the operating parameters of the RF system 120 or the gradient system 118, or to control the view order in which k-space is sampled. In still another example, the data acquisition server 112 may also be employed to process magnetic resonance signals used to detect the arrival of a contrast agent in a magnetic resonance angiography (MRA) scan. By way of example, the data acquisition server 112 acquires magnetic resonance data and processes it in real-time to produce information that is used to control the scan.

The data processing server 114 receives magnetic resonance data from the data acquisition server 112 and processes it in accordance with instructions downloaded from the operator workstation 102. Such processing may, for example, include one or more of the following: reconstructing two-dimensional or three-dimensional images by performing a Fourier transformation of raw k-space data; performing other image reconstruction algorithms, such as iterative or back-projection reconstruction algorithms; applying filters to raw k-space data or to reconstructed images; generating functional magnetic resonance images; calculating motion or flow images; and so on.

Images reconstructed by the data processing server 114 are conveyed back to the operator workstation 102 where they are stored. Real-time images are stored in a data base memory cache (not shown in FIG. 1), from which they may be output to operator display 112 or a display 136 that is located near the magnet assembly 124 for use by attending physicians. Batch mode images or selected real time images are stored in a host database on disc storage 138. When such images have been reconstructed and transferred to storage, the data processing server 114 notifies the data store server 116 on the operator workstation 102. The operator workstation 102 may be used by an operator to archive the images, produce films, or send the images via a network to other facilities.

The MRI system 100 may also include one or more networked workstations 142. By way of example, a networked workstation 142 may include a display 144; one or more input devices 146, such as a keyboard and mouse; and a processor 148. The networked workstation 142 may be located within the same facility as the operator workstation 102, or in a different facility, such as a different healthcare institution or clinic.

The networked workstation 142, whether within the same facility or in a different facility as the operator workstation 102, may gain remote access to the data processing server 114 or data store server 116 via the communication system 117. Accordingly, multiple networked workstations 142 may have access to the data processing server 114 and the data store server 116. In this manner, magnetic resonance data, reconstructed images, or other data may exchanged between the data processing server 114 or the data store server 116 and the networked workstations 142, such that the data or images may be remotely processed by a networked workstation 142. This data may be exchanged in any suitable format, such as in accordance with the transmission control protocol (TCP), the internet protocol (IP), or other known or suitable protocols.

Figure 2B:
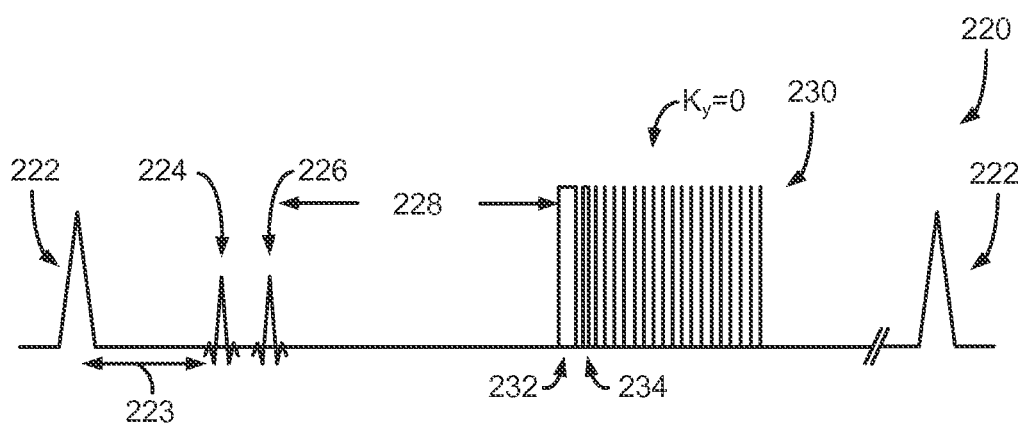
FIGS. 2B and 2C are pulse diagrams of pulse sequences that may be utilized with the imaging process of FIG. 2A.

Referring to FIGS. 2A and 2B, the invention can be implemented with, for example, an MRI system such as described above. Specifically, FIG. 2A is a flow chart setting forth exemplary steps of a method 200 for selective, non-contrast-enhanced, magnetic resonance imaging angiography of arteries and veins. The process starts with the acquisition of two data sets. Specifically, at process block 202 flow-dependent imaging data is acquired and at process block 204, flow independent imaging data is acquired. For example, each of the sets of data may be acquired using, for example, a stack of cardiac-gated two-dimensional (2D) slices acquired, preferably, near the magnet isocenter, with one slice acquired per cardiac interval, such as per RR interval. As will be further described, the flow-independent data can be acquired in a variety of ways. For example, either a 3D or 2D acquisition could be used. Also, it is not necessary to apply a saturation pulse to suppress inflowing spins for the flow-independent data. For example, a 3D trueFISP sequence could be used with no saturation pulses to create a flow-independent MRA.

Specifically, referring to FIG. 2B, a pulse sequence diagram is illustrated for a flow-dependent data acquisition, such as described above with respect to process block 202. As will be described, one desired flow-dependent data acquisition may be performed using quiescent-inflow single-shot (QISS) MRA, such as described in co-pending U.S. application Ser. No. 12/574,856, which is incorporated herein by reference in its entirety. Thus, as illustrated in FIG. 2B, the flow-dependent data acquisition may be a directionally-selective or flow-dependent QISS (FDQISS) technique 220. The FDQISS technique 220 may be cardiac gated based on cardiac waveform 222, for example, timed within an RR interval. Based thereon, for example, 100 milliseconds thereafter or at another desirable interval 223, an in-plane radiofrequency (RF) saturation pulse to suppress signal within the imaging slice 224 is applied. The saturation pulse or pulses are applied in the imaging slice, and also saturation pulse or pulses 226 are applied to venous spins to reduce venous signal flowing into the imaging slice. In this regard, the saturation pulse or pulses 228 may be applied to a slab contiguous with and/or caudal to the imaging slice. In this manner, saturated venous spins and unsaturated arterial spins will flow into the imaging slice over the duration of a selected the quiescent interval ("QI") or quiescent interval time period ("QITP") 228.

The QITP 228 is selected is specifically tailored to coincide with the rapid inflow of arterial blood into a prescribed imaging slice, and so that the zero line of k-space may be acquired during the slow, diastolic inflow of arterial blood into the imaging slice. The QITP is selected based on a desired inflow of unsaturated arterial spins into the imaging slice, such that an improved discrimination of arterial spins is provided in the resultant images. This is even so when the patient's vasculature is significantly impacted by vascular diseases such as peripheral vascular disease ("PVD"). Exemplary values of QITP in this configuration of the pulse sequence are on the order of 250 to 350 milliseconds.

After the QITP 228, readout of the MR signal 230 is performed during the period of slow diastolic flow, for example, using a balanced steady-state free precession (bSSFP) pulse sequence. The readout 230 may be a single-shot readout. This combination of factors ensures that arterial signal is high while background signal is suppressed. Optionally, a fat saturation pulse 232 and/or an alpha/2 preparation 234 may be coupled with the readout 230. As described above, the above-described technique 220 may be completed within another instance of the selected wave 222, for example, an R wave, in the cardiac cycle.

Figure 2C:
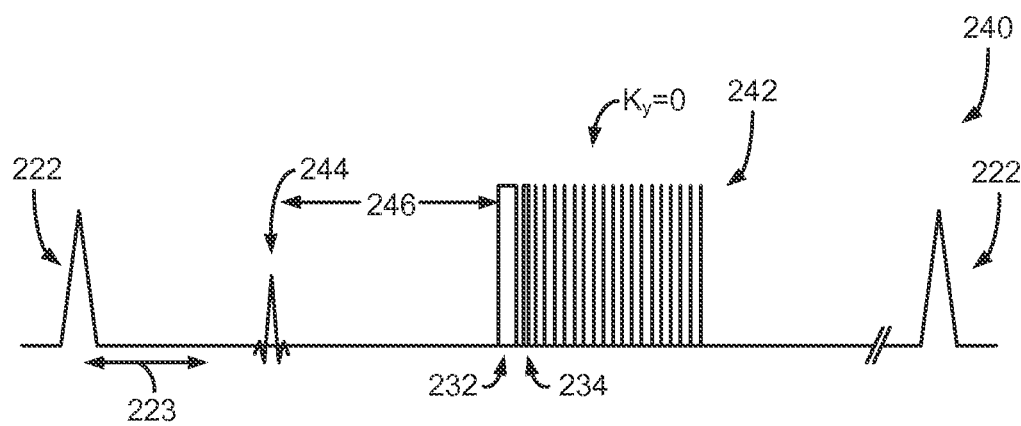

Referring now to FIGS. 2A and 2C, the flow-independent imaging data acquired at process block 204 may be acquired using a pulse sequence 240 that is similar to the QISS-based pulse sequence described above with respect to FIG. 2B, such as including identical or substantially similar geometric and acquisition parameters. However, the flow-independent imaging pulse sequence 240 does not include in-plane RF saturation. In combination with a carefully-designed readout 242, such as a single-shot readout, this renders the technique flow-independent. Consequently, the pulse sequence can be referred to as flow-independent quiescent-interval single shot (FIQISS). In addition to lacking an in-plane RF saturation pulse or pulses, an RF saturation pulse 244 is applied to inflowing arterial spins, rather than to the inflowing venous spins targeted by the tracking saturation pulse 226 of FIG. 2B. Furthermore, a different QITP is selected to control inflow of saturated arterial spins so that arterial signal is suppressed. Consequently, the QITP values for the FDQISS pulse sequence of FIG. 2B and the FIQISS pulse sequence of FIG. 2C may differ. Furthermore, the FIQISS readout 242 may occur in a different phase of the cardiac cycle than with FDQISS readout 230.

Referring again to FIG. 2, once both data sets are acquired, the process continues at process block 206 with registration of the acquired datasets and the selection and application of desired weighting. Specifically, data acquired using the FDQISS pulse sequence of FIG. 2B will produce images that show bright arteries with suppressed signal from veins. On the other hand, data acquired using the FIQISS pulse sequence of FIG. 2C will produce images that show bright veins with suppressed signal from arteries. By weighting the two image sets appropriately at process block 206 a normalization or contrast matching can be achieved between the two different acquisitions. At process block 208, a user may select whether the resulting images reflect arteries or veins and, at process block 210, the FDQISS images and the FIQISS images are subtracted. That is, if at process block 208 the user selects arteries to be reflected in the images, at process bock 212, the FDQISS images are subtracted from the FIQISS images and a set of subtractive images is created at process block 212 in which veins appear bright and arteries dark, with suppression of background signal. Conversely, if at process block 208 the user selects veins to reflected in the images, at process block 212, the FIQISS images are subtracted from the FDQISS images and the set of subtractive images is created at process block 212 in which arteries appear bright and veins dark, again with suppression of background signal. Advantageously, image quality is independent of flow velocity.

It should be noted that images acquired only by using the FIQISS pulse sequence could show bright signal from fluids, such as synovial fluid in the knee joint, and blood vessels. However, a modification of the invention allows fluid signal to be suppressed. While optional in the context of the above process, this modification may be helpful in certain instances where there is a large amount of fluid present. Fluids and venous blood have different T1 relaxation times. For example, the T1 time of fluids is approximately 3 seconds and the T1 relaxation time of venous blood is approximately 1 second. Consequently, one or more additional RF fluid-suppressing pulses (FSP) can be applied so as to improve contrast between veins and fluid based on the difference in their T1 relaxation times. If desired, the FSP can be applied to a different slice from the imaging slice, without affecting the imaging slice. In this case, more than one RR interval elapses between the time that the FSP is applied and the signal is read out from the imaging slice. The longer time interval may be helpful to optimize T1-based contrast between fluids and blood vessels. Phase-based reconstructions may further improve contrast, particularly when the FSP consists of an inversion (180 degree) RF pulse and the wait time is short.

Other modifications may also be advantageous in certain instances. For example, the use of non-Cartesian k-space trajectories, acquiring more than one slice per RR interval, and interleaving the FDQISS and FIQSS acquisitions may be advantageous in certain circumstances. In this case, a multi-shot acquisition may be utilized instead of a single shot acquisition.

The present invention can be used to overcome problem issues presented by thrombus appearing bright in certain MRA images and, consequently, mimicking a patent vessel when it is actually occluded. That is, the present disclosure overcomes this concern by virtue of allowing comparison of signal properties in the arterial and venous image sets. Thrombus has a short T1 relaxation time due to the presence of methemoglobin. Consequently, it will show high signal on the FDQISS images, due to the T1-weighting effect of the in-plane saturation RF pulse, but in a location corresponding to a vein on the FIQISS images.

Figure 3:
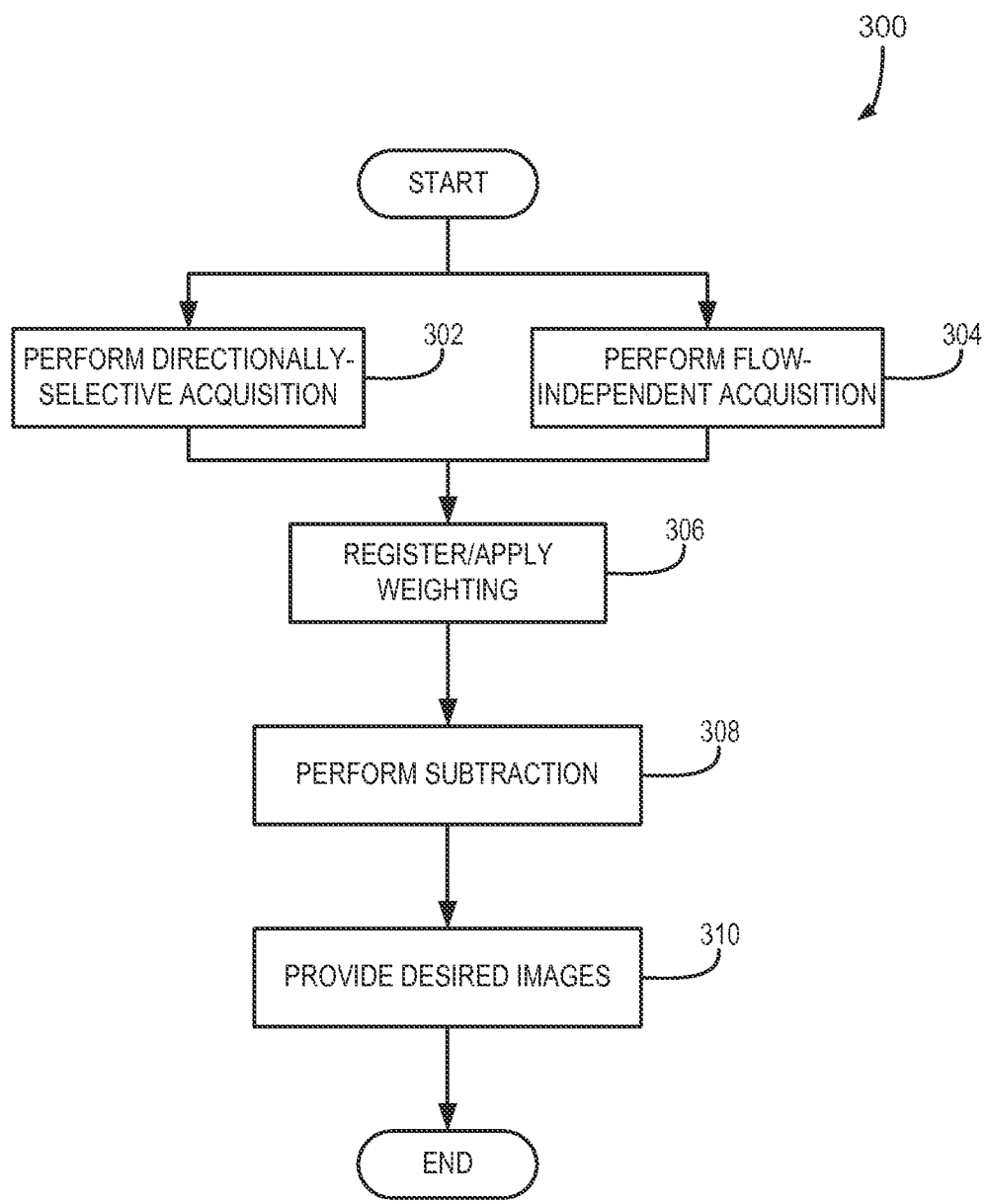
FIG. 3 is a flow chart setting forth the steps of another imaging process in accordance with the present disclosure, for example, using a system such as described with respect to FIG. 1.

Referring to FIG. 3, the above-described techniques may be further adjusted to provide a system and method for flow-independent MRA, acquired with or without contrast enhancement, which selectively depicts arteries or veins. Specifically, the process 300 begins with two acquisitions at process blocks 302 and 304. At process block 302, a directionally-selective 2D acquisition is performed. Also, at process block 304 a flow-independent MRA acquisition technique is performed to acquire data from both arteries and veins.

More particularly, the directionally-selective 2D acquisition uses thin slices and saturation pulses combined with a QITP to selectively and robustly suppress signal from arteries or veins. As will be described, it is contemplated that artery suppression is desired. As a result, a volumetric data set is created from a stack of thin slices using a 2D pulse sequence, which will depict only veins. Arterial signal within each slice is selectively suppressed by the application of one or more out-of-slice radiofrequency (RF) pulses to saturate inflowing arterial spins. These saturating RF pulses may be followed by a selected QITP. The QITP may be selected, for example, on the order of 10 ms to 500 ms, to allow the saturated arterial spins to flow into the slice. The use of thin, 2D slices and a selected QITP ensures that there will be complete replacement of unsaturated in-slice arterial spins with saturated out-of-slice spins, so that the arteries will always appear dark. The slices are typically oriented in a direction roughly orthogonal to the direction of blood flow, which may differ from the orientation of the flow-independent MRA.

As stated, the flow-independent MRA is acquired at process block 304 is designed to depict both arteries and veins. The flow-independent imaging data acquired at process block 304 may be acquired using a pulse sequence that is similar to or based on the QISS-based pulse sequence. At process block 306, the data sets are registered and filtered or weighted. Registration may include scaling and the filtering or weighting can be used to better match intensities of particular tissues, such as background tissue or particular vessels, between the data sets.

Thereafter, a subtraction of the two data sets is performed at process block 308, for example the subtraction may be a pairwise subtraction, to produces data in which the desired vessels, in the above example, only arteries, appear bright. At process block 310, the subtractive data is projected to form angiogram-like images in which the vessels are selectively depicted.

The above-example process can be modified to create flow-independent MR venograms instead of arteriograms. This can be achieved by applying the saturating RF pulses to inflowing venous spins instead of arterial spins during the 2D acquisition. Some other modifications or variations may include the use of various fat suppression, non-Cartesian k-space trajectories, and interleaving the acquisition of the data sets. Additional RF pulses, such as magnetization transfer or inversion pulses, may be applied to change the image contrast. Each 2D image is efficiently acquired as a single shot. However, multiple shots can be used at the expense of scan time. Cardiac gating may be used, as well as respiratory synchronization.

Therefore, a system and method is provided that can depict venous anatomy irrespective of the velocity or pattern of venous blood flow, and is effective even when blood flow is entirely absent. Moreover, by performing subtraction of the FDQISS and FIQISS image sets, images can be created which only show veins or only show arteries.

The present invention has been described in terms of one or more preferred embodiments, and it should be appreciated that many equivalents, alternatives, variations, and modifications, aside from those expressly stated, are possible and within the scope of the invention.

The invention claimed is:

1. A magnetic resonance imaging (MRI) system comprising:
   a magnet system configured to generate a polarizing magnetic field about at least a region of interest (ROI) in a subject arranged in the MRI system;
   a plurality of gradient coils configured to apply a gradient field to the polarizing magnetic field;
   a radio frequency (RF) system configured to apply an excitation field to the subject and acquire MR image data from a ROI;
   a computer system programmed to carry out steps of:
   a) performing a first pulse sequence that directs the MRI system to:
      i) apply at least one RF saturation pulse to a prescribed imaging slice to suppress MR signals in the prescribed imaging slice;
      ii) apply at least one RF saturation pulse to a slice outside the prescribed imaging slice to suppress signal from spins flowing into the prescribed imaging slice from the slice outside the prescribed imaging slice through one of veins and arteries;
      iii) observe a first quiescent inflow time period (QITP) selected to allow a desired inflow of spins flowing into the prescribed imaging slice from the slice outside the prescribed imaging slice through the one of arteries and veins;
      iv) acquire a flow-dependent imaging data set from the prescribed imaging slice following the first QITP;
   b) performing a second pulse sequence that directs the MRI system to acquire a flow-independent imaging data set from the prescribed imaging slice;
   c) subtracting the flow-dependent imaging data and the flow-independent imaging data to create a difference image of the prescribed imaging slice; and a display configured to display the image of the prescribed imaging slice illustrating the at least one of the arteries and the veins as having a bright contrast and another of the arteries and veins as having a suppressed contrast.

2. The system of claim 1 wherein to performing the second pulse sequence in step b) directs the MRI system to:
   i) apply at least one RF saturation pulse to a slice outside the prescribed imaging slice to suppress signal from spins flowing into the prescribed imaging slice from the slice outside the prescribed imaging slice through a one of arteries and veins not saturated in step a)ii);
   ii) observe a second QITP selected to allow a desired inflow of spins flowing into the prescribed imaging slice from the slice outside the prescribed imaging slice through the one of arteries and veins not saturated in step a)ii);
   iii) acquire the flow-independent imaging data set from the prescribed imaging slice following the second QITP.

3. The system of claim 1 further comprising a physiological system configured to monitor a cardiac cycle of the subject and wherein the computer system is further programmed to coordinate step a)iv) and step b)iii) within the cardiac cycle of the subject.

4. The system of claim 3 wherein the computer system is further programmed to perform step a)iv) and step b)iii) to be performed within different portions of the cardiac cycle of the subject.

5. The system of claim 1 wherein the second pulse sequence does not includes applying an RF saturation pulse to the prescribed imaging slice to suppress MR signals in the prescribed imaging slice.

6. The system of claim 1 wherein the computer system is configured to perform the first QITP and the second QITP to have different durations.

7. The system of claim 1 wherein the computer system is configured to perform step c) to include subtracting the flow-dependent imaging data from the flow-independent imaging data to yield a difference image where veins have the bright contrast and arteries have the suppressed contrast.

8. The system of claim 1 wherein the computer system is configured to perform step c) to include subtracting the flow-independent imaging data from the flow-dependent imaging data to yield a difference image where arteries have the bright contrast and veins have the suppressed contrast.

9. The system of claim 1 wherein the computer system is further programmed to perform at least one of registering and weighting the flow-dependent imaging data and the flow-independent imaging data prior to step c).

10. The system of claim 1 wherein the computer system is further programmed to receive a selection of one of arteries and veins to have a bright contrast and another of the arteries and veins as having a suppressed contrast in the difference image.

11. A method for producing an image of a vascular structure of a subject using a magnetic resonance imaging (MRI) system, the method including steps comprising:
   a) performing a first pulse sequence that directs the MRI system to:
      i) apply at least one radio frequency (RF) saturation pulse to a prescribed imaging slice to suppress MR signals in the prescribed imaging slice;
      ii) apply at least one RF saturation pulse to a slice outside the prescribed imaging slice to suppress signal from spins flowing into the prescribed imaging slice from the slice outside the prescribed imaging slice through one of veins and arteries;
      iii) observe a first quiescent inflow time period (QITP) selected to allow a desired inflow of spins flowing into the prescribed imaging slice from the slice outside the prescribed imaging slice through the one of arteries and veins;
      iv) acquire a flow-dependent imaging data set from the prescribed imaging slice following the first QITP; and
   b) performing a second pulse sequence that directs the MRI system to:
      i) apply at least one RF saturation pulse to a slice outside the prescribed imaging slice to suppress signal from spins flowing into the prescribed imaging slice from the slice outside the prescribed imaging slice through a one of arteries and veins not saturated in step a)ii);
      ii) observe a second QITP selected to allow a desired inflow of spins flowing into the prescribed imaging slice from the slice outside the prescribed imaging slice through the one of arteries and veins not saturated in step a)ii);
      iii) acquire a flow-independent imaging data set from the prescribed imaging slice following the second QITP;
   c) subtracting the flow-dependent imaging data and the flow-independent imaging data to create a difference image of the prescribed imaging slice; and
   d) displaying the image of the prescribed imaging slice illustrating the at least one of the arteries and the veins as having a bright contrast and another of the arteries and veins as having a suppressed contrast.

12. The method of claim 11 wherein the second pulse sequence does not includes applying an RF saturation pulse to the prescribed imaging slice to suppress MR signals in the prescribed imaging slice.

13. The method of claim 11 wherein the first QITP and the second QITP have different durations.

14. The method of claim 11 wherein step a)iv) and step b)iii) are coordinated within a cardiac cycle of the subject.

15. The method of claim 14 wherein step a)iv) and step b)iii) are coordinated to be performed at different portions of the cardiac cycle of the subject.

16. The method of claim 11 wherein step c) includes subtracting the flow-dependent imaging data from the flow-independent imaging data to yield a difference image where veins have the bright contrast and arteries have the suppressed contrast.

17. The method of claim 11 wherein step c) includes subtracting the flow-independent imaging data from the flow-dependent imaging data to yield a difference image where arteries have the bright contrast and veins have the suppressed contrast.

18. The method of claim 11 further comprising the step of at least one of registering and weighting the flow-dependent imaging data and the flow-independent imaging data prior to step c).

19. The method of claim 1 further comprising receiving a selection of one of arteries and veins to have a bright contrast and another of the arteries and veins as having a suppressed contrast in the difference image.

20. A method for producing an image of a vascular structure of a subject using a magnetic resonance imaging (MRI) system, the method including steps comprising:
   a) performing a first pulse sequence that directs the MRI system to:
      i) determine a stack of prescribed imaging slices including arteries and veins;
      ii) apply a series of RF saturation pulses to slices outside the each slice in the stack of prescribed imaging slices to suppress signal from spins flowing into the stack of prescribed imaging slices through one of veins and arteries;

iii) observe a first quiescent inflow time period (QITP) selected to allow an inflow of suppressed signals from spins flowing into the stack of prescribed imaging slices through the one of arteries and veins;

iv) acquire a flow-dependent imaging data set from the stack of prescribed imaging slices following the first QITP; and b) repeating step a) without suppressing signal from spins flowing into the stack of prescribed imaging slices through either of the veins or arteries to acquire a flow-independent imaging data set after a second QITP;

c) subtracting the flow-dependent imaging data and the flow-independent imaging data to create a difference image of the stack of prescribed imaging slices; and d) displaying the image of the stack of prescribed imaging slices illustrating the at least one of the arteries and the veins as having a bright contrast and another of the arteries and veins as having a suppressed contrast.

21. The method of claim 20 wherein step a)iv) is performed using a single shot readout.

22. The method of claim 20 wherein the slices outside each slice in the stack of prescribed imaging slices is oriented orthogonal to a direction of blood flow through the one of the arteries and the veins.

23. The method of claim 20 wherein the first QITP and the second QITP have different durations.

24. The method of claim 20 wherein step a) and step b) are coordinated within a cardiac cycle of the subject.

25. The method of claim 24 wherein step a) and step b) are coordinated acquire the flow-dependent imaging data set and the flow-independent imaging data set within different portions of the cardiac cycle of the subject.

26. The method of claim 20 wherein step c) includes a pairwise subtracting of the flow-dependent imaging data and the flow-independent imaging data.

27. The method of claim 20 further comprising the step of at least one of registering and weighting the flow-dependent imaging data and the flow-independent imaging data prior to step c).

* * * * *